United States Patent [19]

Pusineri et al.

[11] 4,433,072

[45] Feb. 21, 1984

[54] MIXTURES OF POLYMERS FOR MEDICAL USE

[75] Inventors: Christian Pusineri, Serezin du Rhone; Jean Goletto, Ecully, both of France

[73] Assignee: Hospal-Sodip, S.A., Meyzieu, France

[21] Appl. No.: 489,707

[22] Filed: Apr. 29, 1983

Related U.S. Application Data

[62] Division of Ser. No. 417,323, Sep. 13, 1982, Pat. No. 4,394,462, which is a division of Ser. No. 103,894, Dec. 17, 1979, Pat. No. 4,408,026.

[30] Foreign Application Priority Data

Dec. 15, 1978 [FR] France .................................. 78 36065

[51] Int. Cl.$^3$ ................................................. C08J 3/00
[52] U.S. Cl. ........................................ 523/105; 523/111; 523/112; 523/113; 524/27
[58] Field of Search ............... 523/105, 111, 112, 113; 524/27

[56] References Cited

U.S. PATENT DOCUMENTS

| | | | |
|---|---|---|---|
| 3,655,553 | 4/1972 | DeWald | 525/404 |
| 3,655,814 | 4/1972 | Rembaum | 525/334 |
| 3,755,218 | 8/1973 | Yen et al. | 525/453 |
| 3,853,804 | 12/1974 | Yen et al. | 260/32.6 N |
| 3,966,521 | 6/1976 | Patton, Jr. et al. | 521/137 |
| 4,042,536 | 8/1977 | Dietrich et al. | 260/29.2 TN |
| 4,116,905 | 9/1978 | Davis | 260/29.6 NR |

*Primary Examiner*—Morton Foelak
*Attorney, Agent, or Firm*—Gerald D. Sharkin; Robert S. Honor; Walter F. Jewell

[57] ABSTRACT

Polymer compositions of a mixture of vinyl chloride polymer and polyurethane with tertiary amine and/or ammonium groups and heparin.

10 Claims, No Drawings

MIXTURES OF POLYMERS FOR MEDICAL USE

This is a division of application Ser. No. 417,323, filed Sept. 13, 1982, now U.S. Pat. No. 4,394,462 which in turn is a division of application Ser. No. 103,894, filed Dec. 17, 1979, now U.S. Pat. No. 4,408,026.

The present invention relates to polymers which can be converted into shaped articles and can be used in the medical field.

It is known that polymers are widely and increasingly used in the medical field for a very large number of application; thus, they are used for all the materials which are to be in contact with blood or other biological liquids; more precisely, the need for such products (referred to as "medical plastics") in the manufacture of storage flasks, blood bags, tubes, probes, cannulae, catheters and all the equipment which is useful either in blood transfusion operations and perfusion operations or in artificial kidney and lung systems, may be mentioned. Polymers with similar properties are sought in other fields in which it is also necessary to bring polymers into contact with a biological liquid, for example milk in the field of nutrition.

The use of polymers based on vinyl chloride has developed fairly well because of various advantages associated with the nature of these products (in particular their moderate cost); unfortunately, polyvinyl chloride itself is not sufficiently flexible, and, if it is desired to plasticise it, the known plasticisers, in particular phthalates, have much too great a tendency to give rise to the phenomena of exudation and especially of leaching, which is disadvantageous because of the risk of accumulation of plasticiser in the biological liquid or the human body. The leaching of polyvinyl chloride plasticisers takes place simply by extraction of these plasticisers when the polymer is in contact with biological liquids.

One object of the present invention is to provide polymers which can be used in prolonged contact with biological liquids, in particular blood, plasma, milk and protein solutions.

A further object of the invention is to provide plastic polymers based on vinyl chloride.

A further object of the invention is to provide polymers plasticised with non-leachable plasticisers.

A further object of the invention is to provide polymers which have been heparin-treated either in bulk or after they have been shaped.

A further object of the invention is to provide heparin-treated polymers which only slowly release the heparin which they contain.

The invention therefore relates firstly to polymer compositions which are characterised in that they comprise a mixture of vinyl chloride polymer and of polyether-urethane with tertiary amine and/or ammonium groups.

The respective proportion of the constituents in the mixture can vary within wide limits; for example, the proportion of polyether-urethane can be 1 to 99% by weight, relative to the total mixture. However, this proportion of polyurethane is preferably between 20 and 60%.

Vinyl chloride polymers which are particularly used are the homopolymers and copolymers having at least 60% by weight of radicals derived from vinyl chloride (that is to say of chloroethylene units —CHCl—CH$_2$—). As copolymers which can more especially be used, there may be mentioned the copolymers of vinyl chloride and vinyl esters, in particular vinyl acetate. Of course, it is also possible to use terpolymers derived from vinyl chloride, a non-ionic and non-ionisable monomer (such as vinyl esters) and an ionic or ionisable monomer (such as maleic acid); the proportion of this latter monomer is generally limited to 20%, preferably to 8%, by weight, relative to all the monomers in the polymer in question.

As polyether-urethanes with tertiary amine and/or ammonium groups, there may be used either polyether-urethanes in which the amine and/or ammonium groups are located in a branch of the main polymer chain, or polyether-urethanes in which the amine and/or ammonium groups are in the main polymer chain.

The polyether-urethanes, with amine and/or ammonium groups, which are used in the invention are preferably polyurethanes derived from polyethers with oxyalkylene groups (it being possible for this oxyalkylene group to be substituted).

In the following text, the letters n, m, p and q are used to denote, respectively:

n—the number of milliequivalents of oxyethylene units —O—CH$_2$—CH$_2$— per 100 g of polyurethane;

m—the number of milliequivalents of tertiary amine groups, which may or may not be salified, per 100 g of polyurethane. The tertiary amine groups, when they are salified, constitute tertiary ammonium groups; the polyurethanes, with ammonium groups, which are used in the invention therefore have either tertiary ro quaternary ammonium groups;

p—the number of milliequivalents of quaternary ammonium groups per 100 g of polyurethane; and q—the number of milliequivalents of ionic groups per 100 g of vinyl chloride polymer.

The nitrogen-containing polyether-urethanes used in the invention and the polymer compositions derived therefrom are therefore such that they preferably satisfy the following relationships:

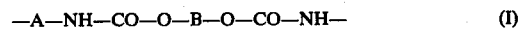

$m + p \geq 0.5$

$p + q \geq (n/100) - 2.5$

The nitrogen-containing polyether-urethanes used in the invention usually comprise a plurality of repeat units of the formula:

$$—A—NH—CO—O—B—O—CO—NH— \quad (I)$$

and of repeat units of the formula:

$$—A—NH—CO—Z—NH— \quad (II)$$

in which formulae:

B is the divalent radical in a macrodiol of the polyether type, of the formula: HO—B—OH, A is the divalent radical in an aliphatic and/or cycloaliphatic and/or aromatic diisocyanate of the formula: O=C=N—A—N=C=O, and

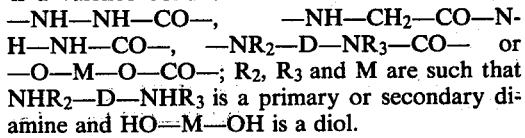

Z is a valence bond or a divalent radical such as: —NH—NH—CO—, —NH—CH$_2$—CO—NH—NH—CO—, —NR$_2$—D—NR$_3$—CO— or —O—M—O—CO—; R$_2$, R$_3$ and M are such that NHR$_2$—D—NHR$_3$ is a primary or secondary diamine and HO—M—OH is a diol.

The units of the formulae I and II are attached to one another in such a way that a terminal carbon atom of one unit is bonded to a terminal nitrogen atom of another unit.

In the invention, the amine and/or ammonium groups can therefore be found, in particular, in the radicals B, A, D or M, but preferably B.

The polyether-urethanes are prepared in the usual manner; the most common process consists in preparing a macrodiisocyanate from a macrodiol and a diisocyanate; the macrodiol used is preferably a poly-(oxyalkylene)-glycol, in particular a poly-(ethylene)-glycol or a poly-(propylene)-glycol. The diisocyanate used is preferably 1,6-diisocyanatohexane, diisocyanatotoluenes, bis-(isocyanatocyclohexyl)-methanes or propanes and bis-(isocyanatophenyl)-methanes or propanes.

These macrodiisocyanates are then coupled by means of coupling agents such as water, hydrazine, aminoacetic acid hydrazide, diamines or diols.

Most frequently, the polyurethane is prepared from reagents which comprise a tertiary amine group either in the macrodiol, or in the diisocyanate, or in the coupling agent. Once the polyurethane has been prepared, the tertiary amine group can be quaternised and this therefore produces a polyurethane with tertiary amine and/or ammonium groups.

If, according to a preferred embodiment, a polyurethane is prepared which has amine and/or ammonium groups located in the polyether (preferably polyoxyalkylene) part of the polyurethane macromolecule, this polyurethane is prepared from a macrodiol containing a tertiary amine group. Thus, according to a variant which is convenient to carry out, this macrodiol is prepared from diols and/or an alkylene oxide and from a diol with a tertiary amine group, such as, for example, alkylbis-(hydroxyalkyl)-amines, in particular N-ethyl-diethanolamine.

Polyether-urethanes with ammonium groups are known from German Application DOS 2,642,616 and from U.S. Pat. Nos. 3,655,814, 3,755,218 and 3,853,804.

The compositions, according to the invention, which have not been heparin-treated are generally soluble in solvents for vinyl chloride polymers, in particular dimethylformamide (DMF), tetrahydrofurane (THF) and also ketones in the case of compositions containing vinyl chloride copolymers.

It is therefore possible to prepare these compositions, and to produce the shaped articles based on these compositions, according to the invention, by evaporating solutions of these compositions; it is also possible to obtain shaped articles comprising a support covered with compositions according to the invention, by coating a shaped article with any material using a liquid coating layer, and then by evaporating this layer, the said liquid coating layer consisting of solutions of compositions according to the invention. A process of this type is particularly suitable for coating the inside of tubes (in particular catheters) but, of course, shaped articles of quite a different form from that of tubes, such as, for example, containers, plane surfaces and the like, may be considered.

It is also possible to obtain shaped articles from a paste which is produced using compositions, according to the invention, containing a blowing agent or an insufficient amount of solvent to dissolve the total amount of the compositions, this mixture of composition and solvent or blowing agent being extruded.

The solvent or blowing agent used must be a solvent or blowing agent both for the vinyl chloride polymer and for the polyurethane with amine or ammonium groups, or alternatively a blowing agent for the mixture of the two polymers combined. Dimethylformamide may be mentioned as the solvent which can be used. In certain cases, it is possible to use lighter and more volatile solvents, such as, for example, acetone, which makes it possible to remove this solvent more easily in order to obtain a composition, according to the invention, in the dry state. When using polyurethanes coupled to ethylene glycol (HO—M—OH mentioned above) and copolymers of vinyl chloride and vinyl acetate, these light solvents can then be used. The pastes based on compositions according to the invention can generally be extruded at a fairly low temperature (below 100° C.).

The materials or shaped articles according to the invention, which consist of compositions according to the invention, have an improved flexibility (compared with the corresponding material without polyurethane), even at ambient temperature; they also have good antistatic properties; they exhibit the advantage of avoiding the use of plasticisers which can exude or leach in contact with biological or physiological liquids. Since the vinyl chloride polymers and the polyether-urethanes with amine and/or ammonium groups are generally compatible, especially when they have been chosen in accordance with the indications given above, the materials or articles which are derived from the compositions according to the invention (in particular the preferred compositions) generally have good mechanical properties and good transparency; moreover, they also have a good compatibility with blood. Their nature enables them to be employed very conveniently. Their permeability to steam renders them of value in many applications requiring this property.

The invention also relates to heparin-treated compositions based on vinyl chloride polymer. The compositions are characterised in that they comprise a vinyl chloride polymer, a polyurethane with an ammonium group, preferably a quaternary ammonium group, and heparin.

In these heparin-treated compositions, the relative proportions of vinyl chloride polymer and of polyurethanes are the same as those indicated above for the compositions which have not been heparin-treated, but these polymers are preferably chosen so that $p_1 - q_1 > 0$, $p_1$ being the product of p multiplied by the percentage by weight of the polyether-urethane in the mixture, divided by 100, and $q_1$ being the product of q multiplied by the percentage by weight of the vinyl chloride polymer, with ionic sites, in the mixture, divided by 100.

As regards the proportion by weight of heparin, it is usually between 0.5 and 35% by weight, relative to all the polymers, and preferably between 1 and 15%.

In the compositions according to the invention and in the following text, when the term heparin is used, it is understood that this term includes the modified heparin forms, for example its salts.

The heparin-treated compositions according to the invention can be obtained by similar processes to those already described for the compositions which have not been heparin-treated. However, since heparin is more generally only slightly compatible or incompatible with polymers based on vinyl chloride alone, it is recommended to introduce the heparin together with, or in the presence of, the polyurethane with ammonium sites, into the vinyl chloride polymer. Thus, according to an advantageous embodiment, a solution of vinyl chloride polymer is mixed with a solution of heparin and of polyurethane, the two solvents for the two solutions being similar or at least miscible. According to another advantageous embodiment, a solution of heparin is added to a solution of a mixture of polyurethane+vinyl chloride polymer. A particularly advantageous process for the preparation of heparin-treated compositions according to the invention, and in particular of shaped compositions, consists in producing a paste and in shaping this paste, for example by extrusion. The paste can be obtained by mixing the constituents with an inadequate amount of solvents to obtain a solution. It is also possible to obtain a paste by partially removing the solvent from a solution. In order to solubilise the heparin or the mixtures of heparin+polyurethane with amine and/or ammonium groups, mixtures of water and dimethylsulphoxide, or of water and diethylene glycol, or of water and dimethylformamide, are preferably used. In order to produce pastes of heparin-treated compositions according to the invention, a solvent or blowing agent for these compositions is advantageously used, for example dimethylformamide or mixtures of water+dimethylformamide or of water+diethylene glycol or of water+dimethylsulphoxide.

With the heparin-treated compositions according to the invention, it is fairly advantageous to employ them with a volatile solvent (for example acetone) in order to be able to evaporate this solvent off without adversely affecting the heparin (in particular by degradation). As indicated above, the compositions, according to the invention, which are derived from vinyl chloride copolymers and from polyurethanes coupled to ethylene glycol are particularly suitable for the use of a volatile solvent in the production of pastes which can be extruded.

In order to obtain a paste of this type, it is generally advantageous to start by forming a solution of the three constituents of the mixture, so as to obtain a very homogeneous mixture, and then, after having removed the solvent, for example by precipitation with a nonsolvent, to add the volatile solvent producing the paste. The preferred volatile solvent is acetone. As the solvent for the heparin-treated ternary mixture, it is preferred to use mixtures of water/aprotic polar solvent, in particular water/DMF, water/DMSO or water/DEG (DMF=dimethylformamide, DMSO=dimethylsulphoxide and DEG=diethylene glycol).

This process can be modified by preparing the first solution of the constituents of the mixture with only the polyurethane and the heparin; in this case, the addition of the vinyl chloride polymer does not have to take place until later, by malaxating all three constituents of the mixture in the pasty state and in the presence of a volatile solvent.

The heparin-treated compositions according to the invention possess a particularly good compatibility with blood and they also have a very good anti-thrombogenic action, in particular because of the very slow leaching of the heparin. Their use for producing articles which are to be employed in contact with blood (tubes, blood bags, artificial vessels and catheters) is therefore particularly recommended. The heparin-treated compositions which can be employed in the form of a paste, and especially in the form of a paste using a volatile solvent, are preferred.

Although, in the above text, consideration has only been given to compositions which have been heparin-treated in bulk, the invention also relates to shaped articles, based on vinyl chloride polymers and on polyurethane containing ammonium sites, preferably quaternary ammonium sites, which have been heparin-treated on the surface. In this case, the amounts of heparin used are greatly reduced.

The following examples, which are given without implying a limitation, illustrate the invention and show how it can be put into effect.

EXAMPLE 1

Preparation of Unquaternised Polyurethane 333 g of N-ethyldiethanolamine and 8.32 g of potassium hydroxide are introduced into a 7,500 cm$^3$ autoclave provided with a nitrogen atmosphere and equipped with a stirring system; the mixture is heated at 95° C. until the solid has completely dissolved. After cooling, the reaction mixture is dehydrated at 80°-82° C. under an absolute pressure of 13 mm Hg, the temperature is then raised to about 111° C. and propylene oxide is injected, the pressure being kept at between 4 and 5 bars. The amount of propylene oxide introduced after 8 hours is: 2,480 g; the reaction mixture is kept at this temperature for a further 2 hours and the unreacted propylene oxide (120 g) is then removed by vacuum distillation. The polyether thus obtained contains 0.936 milliequivalent/gram of tertiary nitrogen. This polyether is neutralised by adding hydrochloric acid until the pH is 6–7, the reaction mixture is then dehydrated by heating at 80° C. under an absolute pressure of 1 to 2 mm Hg and the potassium chloride formed is filtered off.

422.5 g or 4,4'-diisocyanatodiphenylmethane are added all at once, under an inert atmosphere, to 930.7 g of this salified polyether, which has been heated to 80° C., and the mixture is kept at this temperature for 45 minutes, whilst stirring. The resulting macrodiisocyanate is cooled and dissolved in 750 cm$^3$ of dimethylformamide.

A solution of 37.6 g of aminoacetic acid hydrazide in 1,740 g of dimethylformamide is then prepared by heating to 60° C. This solution is cooled, 1,015 g of the previously prepared macrodiisocyanate solution are introduced therein, in the course of 1 hour 45 minutes, and the mixture is then diluted by adding 1,890 g of dimethylformamide. The polyurethane solution thus obtained is poured slowly, and whilst stirring vigorously, into a mixture of 8 kg of ice and 24 kg of water containing 128 g of sodium hydroxide, in order to precipitate the polymer. The latter is filtered off, washed with water until the washings are neutral, dried in vacuo at 40° C. and then dried to constant weight over phosphorous pentoxide at ambient temperature. 682 g of polyurethane, containing 0.583 milliequivalent/g (meq/g) of tertiary nitrogen (acidimetric determination), are thus obtained.

Preparation of the Quaternised Polyurethane 256 g of the polyurethane described above are dissolved in 1,344 g of dimethylformamide, and 85 g of methyl iodide are added to this solution. The mixture is stirred for 15 minutes at ambient temperature and then for 9 hours 30 minutes at 46° C. After cooling, it is run into a mixture of 7.5 kg of ice and 25 kg of water, whilst stirring vigorously; the precipitated polymer is filtered off, washed with water and then with methanol and dried to constant weight as above. The degree of quaternisation, determined by acidimetry, is 100%. The polymer contains 0.538 milliequivalent of quaternary ammonium per gram (meq/g).

EXAMPLE 2

Preparation of Unquaternised Polyurethane 300 g of a polyoxyethylene glycol (marketed under the trademark CARBOWAX 1,500), having a molecular weight of 1,500, are introduced into a 1 liter reactor provided with a nitrogen atmosphere and equipped with a stirring system and a reflux condenser. The glycol is melted and the reaction mixture is then dehydrated at 100° C. under an absolute pressure of 1 mm Hg. Atmospheric pressure is re-established by introducing nitrogen and the temperature is lowered to 80° C. 0.4 g of malonitrile is introduced and 100 g of 4,4'-diisocyanatodiphenylmethane are then introduced 15 minutes later. The temperature of the reaction mixture is kept at 80° C. for 3 hours. The resulting macrodiisocyanate is cooled and dissolved in 250 cm³ of dimethylformamide.

A solution of 23.7 g of aminoacetic acid hydrazide in 1,250 g of dimethylformamide is then prepared. This solution is cooled and a mixture of 258 g of a 65% strength solution, in dimethylformamide, of the macrodiisocyanate prepared in accordance with Example 1, and of 578 g of a 63% strength solution, in dimethylformamide, of the macrodiisocyanate described above at the start of this Example 2, is then run in, in the course of 4 hours. The copolyurethane solution thus obtained is poured slowly, and whilst stirring vigorously, into 30 liters of water containing 600 g of sodium chloride and 120 g of sodium hydroxide, at +5° C., in order to precipitate the polymer. The latter is filtered off, washed with water until the washings are neutral and until the chloride ions have disappeared, dried in vacuo at 40° C. and then dried to constant weight over phosphorus pentoxide at ambient temperature. 460 g of copolyurethane, containing 0.189 milliequivalent/g of tertiary nitrogen and 1,124 meq of oxyethylene units per 100 g of polyurethane, are thus obtained.

Preparation of the Quaternised Copolyurethane 330 g of the copolyurethane which has just been prepared in this way, and 3,300 cm³ of acetone, are introduced into a 5 liter reactor equipped with a stirring system. 19.7 g of methyl iodide are introduced, under a nitrogen atmosphere, the reactor is stoppered and the mixture is stirred for 20 hours at ambient temperature. The polymer is filtered off, washed with acetone and then with ether and dried to constant weight as above. The degree of quaternisation is 100%. The polymer contains 0.184 milliequivalent/g of quaternary ammonium and 1,094 meq of oxyethylene units per 100 g of polyurethane.

EXAMPLE 3

Preparation of Unquaternised Polyurethane 16.7 g of ethylene glycol, 0.4 g of dibutyltin dilaurate and 950 g of dimethylformamide are introduced into a 5 liter reactor provided with a nitrogen atmosphere and equipped with a stirring system and a reflux condenser. The mixture is stirred and 792 g of a 55% strength solution, in dimethylformamide, of the macrodiisocyanate prepared in accordance with Example 1 are run in, in the course of one hour. The temperature of the reaction mixture is raised to 70°–75° C. in the course of one hour and the addition of the macrodiisocyanate solution is terminated slowly. The polyurethane solution thus obtained is poured, whilst stirring vigorously, into 20 liters of water containing 400 g of sodium chloride and 80 g of sodium hydroxide, at +5° C., in order to precipitate the polymer. The latter is filtered off, washed with water until the washings are neutral and the chloride ions have disappeared, dried in vacuo at 40° C. and then dried to constant weight over phosphorus pentoxide at ambient temperature. 450 g of polyurethane, containing 0.599 milliequivalent/g of tertiary nitrogen, are thus obtained.

Preparation of Quaternised Polyurethane

The unquaternised polyurethane prepared above is quaternised in accordance with the technique described in Example 1. The resulting polymer contains 0.561 meq/g of quaternary ammonium. Of course, the tin salts are removed by precipitating the polymer in a non-solvent which, however, is a solvent for the tin salts.

EXAMPLE 4

Preparation of Unquaternised Polyurethane 32.6 g of ethylene glycol, 0.97 g of dibutyltin dilaurate and 2,267 g of dimethylformamide are introduced into a 5 liter reactor provided with a nitrogen atmosphere and eqipped with a stirring system and a reflux condenser.

90% of a mixture containing 676.8 g of a 47% strength solution, in dimethylformamide, of a macrodiisocyanate prepared in accordance with Example 1, and 1,144 g of a 54% strength solution, in dimethylformamide, of a macrodiisocyanate prepared in accordance with the technique described in the first paragraph of Example 2, is run into this solution in the course of 1 hour.

The temperature of the reaction mixture is raised to 70°–75° C. in the course of 1 hour, the addition of the solution of the two macrodiisocyanates is terminated slowly and a solution of 26 g of 4,4'-diisocyanatodiphenylmethane in 80 g of dimethylformamide is then added to the reaction medium. The copolyurethane solution thus obtained is poured, whilst stirring vigorously, into 50 liters of water containing 1,000 g of sodium chloride and 200 g of sodium hydroxide, at +5° C., in order to precipitate the polymer. The latter is filtered off, washed with water until the washings are neutral and the chloride ions have disappeared, then washed with methanol, dried in vacuo at 40° C. and then dried to constant weight over phosphorus pentoxide at ambient temperature. 1,000 g of copolyurethane, containing 0.195 milliequivalent/g of tertiary nitrogen and 1.066 meq/g of oxyethylene units —O—CH$_2$—CH$_2$—, are thus obtained.

Preparation of the Quaternised Copolyurethane 500 g of the copolyurethane prepared at the start of the present example, and 4 liters of methanol, are introduced into a 5 liter reactor equipped with a stirring system. 27.7 g of methyl iodide are introduced, under an argon atmosphere, the reactor is stoppered and the mixture is stirred for 20 hours at ambient temperature. The polymer is filtered off, washed with methanol and dried to constant weight as above.

The degree of quaternisation is 77%. The polymer contains 0.150 milliequivalent/g of quaternary ammonium and 0.042 milliequivalent/g of unsalified tertiary nitrogen.

EXAMPLE 5

900 g of dimethylformamide are introduced into a 2 liter reactor equipped with a stirring system and are cooled to about 3° C. 100 g of a polyvinyl chloride of which the viscosity index is equal to 80 dl/g (measurement carried out according to Encyclopaedia of Polymer Science and Technology, Volume 14, page 374, 1971 edition) are then introduced slowly. The temperature of the mixture is allowed to rise to ambient temperature and stirring is continued until the solid has completely dissolved.

80 g of the solution prepared above, and 5.33 g of a polyurethane, with tertiary amine groups (unsalified and unquaternised), obtained in accordance with Example 1, are introduced into a 125 cm$^3$ flask. The weight ratio of the polyvinyl chloride to the polyurethane is 60/40 and the concentration of the polymers in the solvent is 15.6%. The flask is shaken for 24 hours until the solid has completely dissolved. The resulting solution is filtered and degassed and then run onto a glass plate so as to form an approximately 0.4 mm thick liquid film. This film is dried at 50° C. under an absolute pressure of 200 mm Hg and then detached from its support by dipping in water. The resulting material is transparent and possesses a good tear strength. Its mechanical properties are as follows:

tensile strength: 356 Kg/cm$^2$
elongation at break: 84%

EXAMPLE 6

The mixture of vinyl chloride polymer/polyurethane is prepared under identical conditions to those of Example 5, except that the polyurethane used is the polyurethane containing 0.538 milliequivalent/g of quaternary ammonium groups, obtained in accordance with the technique described in Example 1 (preparation of the quaternised polyurethane).

The resulting material is transparent and possesses a good tear strength and its mechanical properties are as follows:

tensile strength: 427 Kg/cm$^2$
elongation at break: 74%

EXAMPLE 7

The mixture of polyvinyl chloride/polyurethane is prepared under conditions identical to those of Example 5, except that the polyurethane used is the polyurethane containing 0.599 milliequivalent/g of tertiary nitrogen (unquaternised tertiary amine groups), obtained in accordance with the technique described in Example 3.

The resulting material is transparent and possesses a good tear strength.

EXAMPLE 8

The mixture of vinyl chloride polymer/polyurethane is prepared under identical conditions to those of Example 5, except that the polyurethane used is the polyurethane, with quaternary ammonium groups, obtained in accordance with the technique described in Example 3.

The resulting material is transparent and possesses a good tear strength.

EXAMPLE 9

The mixture of vinyl chloride polymer/polyurethane is prepared under identical conditions to those of Example 5, except that the polyurethane used is the polyurethane containing 0.184 milliequivalent/g of quaternary nitrogen (quaternary ammonium groups), obtained in accordance with the technique described in Example 2 (preparation of quaternised polyurethane).

The resulting material is transparent and possesses a good tear strength and its mechanical properties are as follows:

tensile strength: 374 Kg/cm$^2$
elongation at break: 100%

EXAMPLE 10

The mixture of vinyl chloride polymer/polyurethane is prepared under identical conditions to those of Example 5, except that the polyurethane used is the polyurethane containing 0.150 milliequivalent/g of quaternary nitrogen (quaternary ammonium groups) and 0.042 milliequivalent/g of tertiary nitrogen, obtained in accordance with the technique described in Example 4 (preparation of quaternised polyurethane).

The resulting material is transparent and possesses a good tear strength.

EXAMPLE 11

The mixture of polyvinyl chloride/polyurethane is prepared under identical conditions to those of Example 5, except that 3.1 cm$^3$ of a N solution of HCl in dimethylformamide are introduced into the solution of the mixture of polymers, which has the effect of salifying the tertiary amine sites (and of converting them into tertiary ammonium groups). The film obtained in accordance with the technique described in Example 5 is flexible and transparent and possesses a good tear strength.

EXAMPLE 12

The polyvinyl chloride in Examples 5 to 11 is replaced by a vinyl chloride/vinyl acetate copolymer of which the units corresponding to these two monomers are in respective proportions by weight of 85/15, and of which the viscosity index is 54 cm$^3$/g, measured in accordance with AFNOR Standard Specification NF T-51013, and the coefficient K (as defined in Encyclopaedia of Polymer Science and Technology, Volume 14, pages 374-5, 1971 edition) is equal to about 46.

Similar results to those of Examples 5 to 11 are obtained, that is to say that the resulting material (based on a mixture of vinyl chloride polymer and of polyurethane with amine and/or quaternary ammonium groups), in the form of a flexible and transparent film, possesses good mechanical properties, in particular a good tear strength.

EXAMPLE 13

The vinyl chloride polymer used is a vinyl chloride/vinyl acetate/maleic acid terpolymer. The repeat units corresponding to these three monomers are in respective proportions by weight of 84.5/14.4/1.1 (0.189 meq/g of acid groups). This polymer has a molecular weight which is such that its viscosity index (according to AFNOR Standard Specification NF-51013) is about 55 cm$^3$/g and its coefficient K (as defined in Encyclopaedia of Polymer Science and Technology, Volume 14, pages 374-5, 1971 edition) is equal to about 46.

The technique described in Example 5 is then repeated, the vinyl chloride polymer described being replaced by this terpolymer, and each of the unquaternised polyurethanes and each of the salified or quaternised polyurethanes described in each of Examples 1 to 4 being used successively as the polyurethane.

This gives transparent flexible films possessing good mechanical properties, in particular a good tear strength.

EXAMPLE 14

405 g of dimethylformamide are introduced into a reactor equipped with a stirring system, the dimethylformamide is stirred and 90 g of the polyurethane containing 0.150 milliequivalent/g of quaternary ammonium and 0.042 milliequivalent/g of tertiary nitrogen, obtained in accordance with the technique described in Example 4 (preparation of quaternised polyurethane), and then 45 g of the terpolymer used in Example 13, are introduced slowly. Stirring is continued until the solid has completely dissolved, the concentration of the polymers in the solvent than being 25%.

A solution of 15 g heparin (in the form of the sodium salt) in 33 cm³ of water is prepared at the same time and this solution is poured slowly into 48 cm³ of diethylene glycol. The resulting homogeneous solution is poured dropwise, in the course of one hour, into the mixture of polyurethane and vinyl chloride copolymer.

The resulting composition is run slowly into six liters of ethyl ether, whilst stirring vigorously, in order to precipitate the heparin-treated polymer. This polymer is filtered off, washed with ether and dried to constant weight (143.7 g) in an oven, in vacuo, at 50° C., under an absolute pressure of 200 mm Hg.

60 g of the heparin-treated composition prepared above are introduced into a malaxator and 35 cm³ of acetone are added in small portions. Malaxation is continued until a homogeneous paste is obtained. The paste thus obtained, which contains 27% of acetone, is extruded through a sector die producing a thin tube. Extrusion is carried out at 70°–80° C. under a pressure of 470 to 580 bars, the speed at which the tube leaves the die being about 35 cm/minute. The tube is then chopped and the pieces of extruded tube are dried for three days in the vertical position and in an ambient atmosphere, and then under an absolute pressure of 200 mm Hg at 50° C. The catheters thus prepared have an external diameter of 1.9 mm and a wall thickness of 0.2 mm; when brought into contact with freshly sampled dog's blood, they do not cause coagulation during the period of the experiment, which was one hour.

EXAMPLE 15

50 g of polyurethane with quaternary ammonium groups (prepared in accordance with Example 2) are mixed with 50 g of polyvinyl chloride. The mixture is dissolved in 400 g of dimethylformamide at 23° C., whilst stirring.

Furthermore, a solution is prepared using 20 g of heparin (in the form of the sodium salt) and 35 g of water and then 175 g of diethylene glycol.

The heparin solution is then added to the solution of the polymer mixture. A solution of a heparin-treated polymer composition, according to the invention, is thus obtained.

This solution is used on the one hand, for producing films, and, on the other hand, for producing a catheter.

Preparation of a Film

The solution of the heparin-treated polymer composition is run onto a glass plate so as to form a liquid film of dimensions 25 cm × 30 cm × 0.1 cm. This is dried for 12 hours at 50° C. under an absolute pressure of 200 mm Hg. It is washed with water and dried again in the same manner.

Preparation of the Catheter

A glass rod of length 25 cm and diameter 3 mm is dipped in the solution of the heparin-treated polymer composition. It is left to drain at ambient temperature for one hour and then dried at 50° C. for one hour under an absolute pressure of 200 mm Hg. These coating operations are repeated four times and the rod is then finally dried for 12 hours at 50° C. under a reduced pressure of 200 mm Hg (absolute pressure).

When brought into contact with freshly sampled dog's blood, neither the film nor the catheter causes coagulation of the blood during the period of the experiment (one hour).

EXAMPLE 16

Example 15 is repeated, replacing the polyvinyl chloride on the one hand by a vinyl chloride/vinyl acetate copolymer, such as that used in Example 12, and on the other hand by a terpolymer such as that used in Example 13.

Films and catheters which do not cause coagulation of the blood are obtained in the same manner.

EXAMPLE 17

17(a)—Preparation of a macrodiisocyanate from a polyoxy propylene glycol with tertiary amine groups salified by HCl 385.7 g of a salified polyether, prepared according to example 1, are introduced under a nitrogen atmosphere into a 2000 cm³ reactor equipped with a stirring system and a reflux condenser. The salified polyether is dehydrated for one hour, at 100° C., under an absolute pressure of 1 mmHg. Then the temperature is lowered to 80° C. and atmospheric pressure is re-established by introducing nitrogen.

188.2 g of bis(-4-isocyanato cyclohexyl)methane are added, in the molten state and all at once, to the salified polyether. The reaction mixture is kept at 80° C. for 50 hours, whilst stirring. The resulting macrodiisocyanate is cooled and dissolved in 325 cm³ of dimethylformamide.

17(b)—Preparation of a macrodiisocyanate from a polyoxyethylene glycol 601 g of a polyoxyethylene glycol (marketed under the trademark CARBOWAX 1,500), having a molecular weight of 1,500, are introduced in an apparatus identical to that above and in the same manner. The glycol is melted and dehydrated at 100° C. under an absolute pressure of 1 mmHg. Then atmospheric pressure is re-established by introducing nitrogen and the temperature is lowered to 80° C.

220.1 g of bis(-4 isocyanato cyclohexyl)methane are added, in the molten state and all at once, to the polyether. The reaction mixture is kept at 80° C. for 8 hours, whilst stirring. The resulting macrodiisocyanate is cooled and dissolved in 465 cm³ of dimethylformamide.

17(c)—Preparation of a polyurethane with salified tertiary amine groups 3063 g of dimethylformamide and 32.97 g of 1-2diaminopropane are introduced under a nitrogen atmosphere in a 5,000 cm$^3$ reactor equipped with a stirring system and a reflux condenser.

This solution being at room temperature, 80% of a mixture of 863.1 g of a 65% strength solution, in dimethylformamide, of the macrodiisocyanate prepared in accordance with 17(a), and of 440.64 g of a 65% strength solution, in dimethylformamide, of the macrodiisocyanate prepared in accordance with 17(b), is then run in, in the course of 15 minutes. The rest of the mixture of the two macrodiisocyanates is added for 90 minutes. The reaction mixture is then kept under nitrogen atmosphere for 15 hours, whilst stirring.

⅔ of the polyurethane solution thus obtained is poured slowly, whilst stirring, into 30 liters of water containing 600 g of sodium chloride, at 5° C., in order to precipitate the polymer. The latter is filtered off, washed with water until the chloride ions have disappeared and then dried in vacuo at 30° C.

211 g of copolyurethane, containing 0.204 milliequivalent/g of salified tertiary amine and 10.61 milliequivalent/g of oxyethylene units, are thus obtained.

17(d)—Preparation of a polyurethane with tertiary amine groups

⅔ of the solution of copolyurethane prepared in 17(c) are poured slowly into 60 liters of water containing 1,200 g of sodium chloride and 240 g of sodium hydroxyde, at 5° C., in order to precipitate the polyether and to liberate the amine groups. The product is dried by lyophilisation.

590 g of copolyurethane, containing 0.206 meq/g of tertiary amine groups, are thus obtained.

17(e)—Preparation of the quaternised polyurethane 188 g of unquaternised polyurethane prepared in 17(d) are quaternised in accordance with the technique described in example 4, methanol being replaced by acetone.

183 g of dried polymer, containing 0.2 meq/g of quaternary ammonium, are thus obtained.

EXAMPLE 18

12.5 g of polyurethane with quaternary ammonium groups (prepared in accordance with example 17(e) are mixed with 12.5 g of polyvinyl chloride described in example 5. The mixture is dissolved in 290 cm$^3$ of dimethylformamide, whilst stirring, at 23° C. for 3 hours and then for one hour at 80° C. The resulting solution is filtered and degassed and then run onto a glass plate so as to form an approximately 1 mm thick liquid film. This film is dried at 50° C. under an absolute pressure of 200 mmHg and then detached from its support by dipping in water. The resulting material is transparent and possesses a good tear strength. Its mechanical properties are as follows:
 tensile strength: 370 kg/cm$^2$
 elongation at break: 270%

EXAMPLE 19

A film from a solution of polyvinyl chloride and polyurethane with tertiary amine groups (obtained in accordance with example 17(d) is prepared under identical conditions to those of example 18. The resulting material is transparent and possesses a good tear strength:
 tensile strength: 310 kg/cm$^2$
 elongation at break: 230%

EXAMPLE 20

A film is prepared under identical conditions to those of example 18 from a solution of polyvinyl chloride and polyurethane with tertiary amine groups, salified by hydrochloric acid (obtained in example 17(c)). The resulting film is transparent and possesses a good tear strength:
 tensile strength: 300 kg/cm$^2$
 elongation at break: 195%

EXAMPLE 21

The polyvinyl chloride in examples 18 to 20 is replaced by the vinyl chloride/vinyl acetate/maleic acid terpolymer, described in example 13.

Similar results to those of examples 18 to 20 are obtained, that is to say that the resulting materials (with amine and/or ammonium groups, prepared in accordance with example 17) in the form of flexible and transparent films, possesses good mechanical properties, in particular a good tear strength.

EXAMPLE 22

12.5 g of polyurethane with quaternary ammonium groups (prepared in accordance with example 17(e) are mixed with 12.5 g of vinyl chloride/vinyl acetate/maleic acid terpolymer described in example 13. The mixture is dissolved in 100 g of dimethylformamide at 100° C. for 2 hours, whilst stirring.

Furthermore, a solution is prepared using 5 g of heparin (in the form of the sodium salt) and 8.75 g of water and then 43.8 g of diethylene glycol.

The heparin solution is then added to the solution of the polymer mixture which is at room temperature. A solution of a heparin-treated polymer composition, according to the invention, is thus obtained.

This solution is used for producing a film.

Preparation of a Film

The solution of the heparin-treated polymer composition is run onto a glass plate so as to form a liquid film of dimensions 20 cm×30 cm×0.1 cm. This is dried for 24 hours at 50° C. under an absolute pressure of 200 mmHg. It is washed with ether and dried again in the same manner. The resulting film contains 16.6% of heparin.

Coagulation Test with the Resulting Film

Membranes with a diameter of 12 cm are cut in the heparinated film obtained above. After folding these membranes are put into glass cones and they match with the shape of the latter. Then membrane-cones are filled with physiological liquid (water with 9 g/l of NaCl) and the temperature of the latter is kept at 37° C. In each cone the physiological liquid is replaced by 2 cm$^3$ of freshly sampled human venous blood. This blood coagulates after a contact of 5 minutes and 30 seconds with the glass. No coagulation takes place after a contact of 90 minutes with the heparinated membranes.

EXAMPLE 23

In example 22 the terpolymer is replaced by the polyvinyl chloride described in example 5. Films are obtained in the same manner and no coagulation takes place with such films.

EXAMPLE 24

The film prepared in example 18, of which the swelling capacity is 15% in water and is 40% in a mixture of ethanol/water (50%—50% by volume), is immersed in 250 cm³ of a solution water/ethanol (50%—50% by volume) of 3% by weight of heparin (in the form of sodium salt), for 16hours, at 50° C. The film is then washed with water and dried at 50° C., for 10 hours, under 200 mmHg.

The resulting film contains about 2% by weight of heparin.

EXAMPLE 25

90 g of dimethylformamide are introduced in a reactor equipped with a stirring system, and 10 g of polyurethane containing 0.189 meq/g of tertiary nitrogen groups (prepared in accordance with example 2) are introduced slowly in the reactor. After dissolution, it is run into 2.55 cm³ of a N solution of hydrochloric acid in order to salify the polyurethane and then 5 g of the terpolymere of example 13 are added. The mixture is stirred until it has completely dissolved.

A solution is prepared, containing 1.67 g of heparin (in the form of its sodium salt), 2.9 cm³ of water and 14.55 g of diethylene glycol. This solution is added in the course of 30 minutes to the mixture of salified polyurethane and of the terpolymer of vinyl chloride.

The heparinated solution is filtered, degassed and then run onto a glass plate so as to form a liquid film of dimensions 25 cm×30 cm×0.1 cm. This is dried at 50° C., for 24 hours, under an absolute pressure of 200 mmHg. The resulting film is homogeneous, flexible and transparent.

No coagulation takes place with this film in course of 90 minutes, under the same conditions as those of example 22.

What is claimed is:

1. Polymer compositions, useful especially in the medical field, consisting of a mixture of vinyl chloride polymer and a polyether—urethane with tertiary amine and/or ammonium groups and heparin, with the porportion of the polyether—urethane being from 1 to 99% by weight, relative to the total mixture.

2. The polymer compositions according to claim 1 wherein the ammonium groups are quaternary ammonium groups.

3. Composition according to claim 1, characterised in the at the proportions of polyurethane is between 20 and 60% by weight.

4. Compositions according to claim 1 characterized in that the vinyl chloride polymer comprises at least 60% by weight of chloroethylene units.

5. Compositions according to claim 1 characterised in that the vinyl chloride polymer is a vinyl chloride homopolymer or a vinyl chloride/vinyl ester copolymer.

6. Compositions according to claim 1, characterised in that the polyether-urethanes are polyurethanes comprising oxyalkylene groups.

7. Compositions according to claim 1 characterised in that they satisfy: $m+p \geq 0.5$ and $p+q \geq n-2.5$, the letters n, m, p and q respectively denoting:
   n: the number of milliequivalents of oxethylene units $-O-CH_2-CH_2-$ per 100 g of polyurethane,
   m: the number of milliequivalents of tertiary amine groups, which may or may not be salified, per 100 g of polyurethane,
   p: the number of milliequivalents of quaternary ammonium groups per 100 q of polyurethane, and
   q: the number of milliequivalent of ionic groups per 100 g of vinyl chloride polymer.

8. Compositions according to claim 1, characterised in that the polyether-urethanes comprise a plurality of repeat units of the formula:

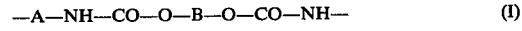

and of repeat units of the formula:

in which formulae:
   B is the divalent radical in macrodiol of the polyether type, of the formula: HO—B—OH,
   A is the divalent radical in an aliphatic and/or cycloaliphatic and/or aromatic diisocyanate of the formula: O=C=N—A—N=C=O, and
   Z is a valence bond or a divalent radical such as: —NH—NH—CO—, —NH—CH₂—CO—NH—NH—CO—, —NR₂—D—NR₃—CO or —O—M—O—CO—; R₂, R₃ and M are such that NHR₂—D—NHR₃ is a primary or secondary diamine and HO—M—OH is a diol.

9. Compositions according to claim 1 characterised in that the proportion of heparin is between 1 and 15%, relative to the polymers.

10. Compositions according to claim 7, characterised in that $p_1-q_1>0$ and in that the proportion of herparin is between 0.5 and 35% by weight relative to all the polymers, $p_1$ being the product of p multiplied by the percentage by weight of the polyurethane in the mixture, divided by 100, and $q_1$ being the product of q multiplied by the percentage by weight of the of the vinyl chloride polymer, with ionic sites, in the mixture, divided by 100.

* * * * *